United States Patent [19]

Wedlock et al.

[11] Patent Number: 5,711,956
[45] Date of Patent: Jan. 27, 1998

[54] SOLID INSECTICIDAL FORMULATION

[75] Inventors: David John Wedlock, Tarporley; Jonathan Mark Woodburn, Sittingbourne, both of England

[73] Assignee: American Cyanamid Company, Madison, N.J.

[21] Appl. No.: 457,893

[22] Filed: Jun. 1, 1995

Related U.S. Application Data

[63] Continuation of Ser. No. 351,964, Dec. 8, 1994, abandoned.
[51] Int. Cl.⁶ ............................. A01N 25/10; A01N 25/12
[52] U.S. Cl. ............................. 424/409; 424/43; 424/419
[58] Field of Search .......................... 514/521, 531, 514/772.3; 424/409

[56] References Cited

U.S. PATENT DOCUMENTS 5,208,030  5/1993  Hoy et al. ............................. 424/409

FOREIGN PATENT DOCUMENTS 0 107 296  5/1984  European Pat. Off. ...... C07C 121/75
0415688    3/1991  European Pat. Off. .
2139893   11/1984  United Kingdom .
9408455   10/1993  WIPO .

Primary Examiner—Peter F. Kulkosky
Attorney, Agent, or Firm—Charles F. Costello, Jr.

[57] ABSTRACT

A solid formulation which comprises polyvinylpyrrolidone and a pyrethroid insecticide, for example alpha-cypermethrin, is disclosed for use in the treatment of animals, for example cattle. Also disclosed are uses of the solid formulation and methods which use the solid formulation in the treatment of animals.

44 Claims, No Drawings

SOLID INSECTICIDAL FORMULATION

This is a continuation of application Ser. No. 08/351,964 filed on Dec. 8, 1994, now abandoned.

The present invention relates to a solid insecticidal formulation and, more particularly, relates to the use of such a formulation in the treatment of animals.

Animals, for example cattle, need to be periodically externally treated with an insecticide in order to combat ectoparasitic pests. One widely used method of contacting animals with an insecticide involves dispersing the insecticide in water in a large tank and then immersing the animals in the liquid in the tank.

Concentrated liquid insecticidal formulations are often used for delivering an insecticide to the water in the tank. However, liquid formulations in the form of emulsifiable concentrates contain a very high proportion of organic solvent (often up to 80 percent) which are increasingly coming under scrutiny for their effect on the environment; emulsion concentrates have a higher water content but still contain organic solvents. Suspension concentrates, another water-based liquid form, are often viscous giving rise to handling problems and loss of active ingredient through retention in the packaging.

A further problem associated with some liquid formulations when used in a tank in which animals are immersed is that of the loss of active ingredient by adsorption to the animals (known as "stripping"). This necessitates replenishment of the tank with active ingredient at shorter intervals than would otherwise be required.

It is an object of the present invention to provide an insecticidal formulation for use in the treatment of animals which is easy to handle and transport, is highly active and has a low susceptibility to stripping.

According to the invention, there is provided a solid formulation which comprises polyvinylpyrrolidone and a pyrethroid insecticide for use in the treatment of animals.

The invention extends to an aqueous dispersion prepared by dispersing a solid formulation which comprises polyvinylpyrrolidone and a pyrethroid insecticide in water for use in the treatment of animals.

The invention extends to the use of polyvinylpyrrolidone and a pyrethroid insecticide for the preparation of a solid formulation for the treatment of animals.

The invention extends to the use of a solid formulation which comprises polyvinylpyrrolidone and a pyrethroid insecticide for the preparation of an aqueous dispersion for the treatment of animals.

The invention extends to the use of an aqueous dispersion prepared by dispersing a solid formulation which comprises polyvinylpyrrolidone and a pyrethroid insecticide in water for the treatment of animals.

The invention extends to a method of treating animals, the method comprising administering to the animals a liquid formulation prepared by dispersing a solid formulation which comprises polyvinylpyrrolidone and a pyrethroid insecticide in water.

The invention extends to a method of combating insects associated with animals, the method comprising treating the animals with a liquid formulation prepared by dispersing a solid formulation which comprises polyvinylpyrrolidone and a pyrethroid insecticide in water.

The solid formulation of polyvinylpyrrolidone and pyrethroid insecticide has, surprisingly, been found to be highly advantageous in the treatment, particularly the therapeutic treatment, of animals. For example, a dispersion of the solid formulation has been found to have unexpectedly high insecticidal activity and a low susceptibility to stripping.

Preferably, the animals are treated against acarid pests. The acarid pests may be ticks.

Preferably, the animals are treated against ectoparasites.

The animals are preferably mammals. The animals are preferably bovine.

Animals, for example cattle, are often treated with an insecticide by immersing the animals in a liquid which includes the insecticide. The liquid is suitably held in a receptacle known as a "dip" tank.

The invention extends to a method of delivering an insecticide to a liquid in a receptacle, for example a dip tank, the method including the step of dispersing a solid formulation which comprises polyvinylpyrrolidone and a pyrethroid insecticide in receptacle liquid.

Preferably, in the method, said receptacle liquid is present in the receptacle prior to the step of dispersing said solid formulation in said receptacle liquid.

The invention extends to a receptacle for immersing animals, the receptacle containing a liquid insecticidal dispersion prepared by dispersing a solid formulation which comprises polyvinylpyrrolidone and a pyrethroid insecticide in water.

A broad range of pyrethroid insecticides for use in the present invention are disclosed in the following publications: U.K. Patent Application No. 1 413 491 (NRDC), European Patent Application. No. 22382 (FMC), European Patent Application No. 107296 (ICI), U.K. Patent Application No. 1 565 932 (Bayer), U.K. Patent Application No. 1 439 615 (Sumitomo), U.K. Patent Application No. 1 560 303 (Sumitomo), U.K. Patent Application No. 2 013 206 (Sumitomo), and U.K. Patent Application No. 2 064 528 (Shell).

Examples of commercial pyrethroid insecticides for use in the present invention include: 5-benzyl-3-furylmethyl(E)-(1R)-cis-2,2-dimethyl-3-(2-oxothiolan-3-ylidenemethyl ) cyclopropanecarboxylate; permethrin (3-phenoxybenzyl (1RS)-cis-trans-3-(2,2-dichlorovinyl)-2,2-dimethylcyclopropanecarboxylate); fenpropathrin ((RS)-α-cyano-3-phenoxybenzyl 2,2,3,3-tetramethylcyclopropanecarboxylate); esfenvalerate ((S)-α-cyano-3-phenoxybenzyl(S)-2(4-chlorophenyl)-3-methylbutyrate); fenvalerate ((RS)-cyano-3-phenoxybenzyl (RS)-2-(4-chlorophenyl)-3-methylbutyrate); cyfluthrin ((RS)-α-cyano-4-fluoro-3-phenoxybenzyl(1RS)-cis-trans-3-(2,2-dichlorovinyl)-2,2-dimethylcyclopropanecarboxylate); beta-cyfluthrin (a reaction mixture comprising two enantiomeric pairs in approximate ratio 1:2, i.e. (S)-α-cyano-4-fluoro-3-phenoxybenzyl(1R)-cis-3-(2,2-dichlorovinyl)-2,2-dimethylcyclopropanecarboxylate and (R)-α-cyano-4-fluoro-3-phenoxybenzyl(1S)-cis-3-(2,2-dichlorovinyl)-2,2-dimethylcyclopropanecarboxylate with (S)-α-cyano-4-fluoro-3-phenoxybenzyl (1R)-trans-3-(2,2-dichlorovinyl))-2,2-dimethylcyclopropanecarboxylate and (R)-α-cyano-4-fluoro-3-phenoxybenzyl(1S)-trans-3-(2,2-dichlorovinyl)-2,2-dimethylcyclopropanecarboxylate); lambda-cyhalothrin (a reaction product comprising equal quantities of (S)-α-cyano-3-phenoxybenzyl(Z)-(1R)-cis-3-(2-chloro-3,3,3-trifluoropropenyl)-2,2-dimethylcyclopropanecarboxylate and (R)-α-cyano-3-phenoxybenzyl(Z)-(1S)-cis-3-(2-chloro-3,3,3-trifluoropropenyl)-2,2-dimethylcyclopropanecarboxylate); cyhalothrin ((RS)-α-cyano-3-phenoxybenzyl(Z)-(1RS)-cis-3-(2-chloro-3,3,3-trifluoropropenyl)-2,2-dimethylcyclopropanecarboxylate); deltamethrin ((S)-α-cyano-3-phenoxybenzyl(1R)-cis-3-(2,2-dibromovinyl)-2,2-dimethylcyclopropanecarboxylate); cypermethrin ((RS)-α-cyano-3-phenoxybenzyl(1RS)-cistrans-3-(2,2-dichlorovinyl)-1,1-dimethylcyclopropanecarboxylate); and alpha-cypermethrin (a racemate comprising (S)-α-cyano-3-phenoxybenzyl(1R)-cis-3-(2,2-dichlorovinyl)-2,2-dimethylcyclopropanecarboxylate and (R)-α-cyano-3-phenoxybenzyl(1S)-cis-3-(2,2-dichlorovinyl)-2,2-dimethylcyclopropanecarboxylate).

Preferably, said pyrethroid insecticide for use in the invention is of general formula:

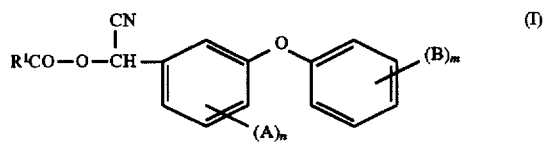
(I)

where A and B independently represent a halogen atom or a methyl group; n is 0, 1 or 2; m is 0, 1 or 2; and $R^1$ represents a group of general formula:

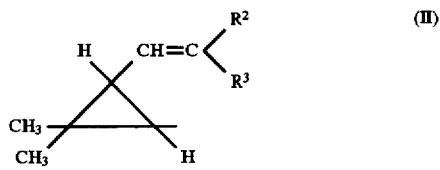
(II)

where $R^2$ and $R^3$ independently represent a hydrogen or halogen atom, or an optionally substituted $C_{1-4}$ alkyl group; or $R^1$ represents a group of general formula:

(III)

where $R^4$ represents a phenyl group optionally substituted by one or more, substituents independently selected from halogen atoms, or $C_{1-4}$ alkyl, $C_{1-4}$ alkylthio, $C_{1-4}$ alkoxy, nitro and methylenedioxy groups.

Preferably, A represents a halogen atom. A preferred halogen atom is a fluorine or chlorine atom, with a fluorine atom being especially preferred.

Preferably, B represents a halogen atom. A preferred halogen atom is a fluorine or chlorine atom.

Preferably, n is 0 or 1. Where n is 1, preferably said atom or group A is substituted in the 4-position relative to the cyanomethyl group in the compound of general formula I.

Preferably, m is 0.

Where $R^1$ represents a group of general formula II, $R^2$ and $R^3$ may independently represent a halogen atom or an optionally substituted $C_{1-2}$ alkyl group. Preferably, $R^2$ and $R^3$ independently represent a bromine or chlorine atom or a trifluoromethyl group. Where $R^2$ and $R^3$ each represent a halogen atom, $R^2$ and $R^3$ preferably represent the same halogen atom. Where $R^2$ represents a trifluoromethyl group, $R^3$ preferably represents a chlorine atom.

Where $R^1$ represents a group of general formula III, $R^4$ preferably represents a phenyl group optionally substituted by one or more halogen atoms. Preferred halogen atoms include fluorine and chlorine atoms. $R^4$ preferably represents a 4-substituted phenyl group and, more preferably, represents a phenyl group substituted by a chlorine atom. Most preferably, $R^4$ represents a 4-chlorophenyl group.

Preferably, said pyrethroid insecticide is alpha cypermethrin.

The pyrethroid insecticide may be prepared using known processes, for example, as described in the aforementioned patent publications.

The solid formulation may be prepared by dissolving polyvinylpyrrolidone and at least one pyrethroid insecticide in a solvent, followed by removal of the solvent from the resulting solution to yield the solid formulation.

The solvent selected for use in the process for the preparation of the formulation must be one in which both the pyrethroid insecticide and polyvinylpyrrolidone are sufficiently soluble. Such solvents are readily identifiable by routine experimentation. Examples of suitable solvents include haloalkanes, preferably having from one to eight carbon atoms, more preferably from one to four carbon atoms, ketones, preferably acetone and alcohols, preferably the lower alcohols having from one to eight carbon atoms, more preferably one to four carbon atoms. Preferred solvents are chloroalkanes having from one to four carbon atoms, with dichloromethane and trichloromethane being especially preferred.

Removal of the solvent may be effected by methods well known to a person skilled in the art, for example by allowing the solution of the pyrethroid and polyvinylpyrrolidone to stand and allowing the solvent to evaporate. Preferably, the solvent is removed from the solution by evaporation at a pressure below atmospheric pressure. Evaporation of the solvent at a pressure below atmospheric pressure may be effected using conventional vacuum drying techniques and apparatus at a pressure down to the minimum operating pressure of the apparatus. Solvent removal is preferably effected at a pressure below 400mbar ($4 \times 10^4$ $Nm^{-2}$). Alternatively, solvent removal may be effected by conventional spray drying techniques. As a further alternative, the solvent may be removed by treating the solution with a further solvent to cause the pyrethroid and polyvinylpyrrolidone to precipitate. Such further solvents are readily identified by routine experiment. One example of such a solvent is hexane.

Once the solvent has been removed, the resulting solid formulation may be pressed (without heating) into tablet form or agglomerated into granules. Alternatively, the solid formulation may be crushed or ground to reduce the particle size and so aid dispersion.

Preferably, the solid formulation is prepared by co-extruding a pyrethroid insecticide with polyvinylpyrrolidone, subsequently cooling the extrudate until brittle, and then milling.

Milling is a process of, primarily, crushing, grinding and pulverising, which produces minute granules of extrudate. If desired, the milled extrudate can be pressed (without heating) into tablet form in conjunction with typical tabletting ingredients which aid dispersal, or agglomerated into granules without loss of the rapid dispersal characteristics.

The cooling of the extrudate should be carried out straight after the extrusion process and may be effected in any suitable, conventional manner. It has been found useful to run the extrudate onto a roller assembly which is cooled, for example by using chilled water or optionally a chilled water-antifreeze mixture. The extrudate is preferably cooled rapidly to a temperature in the range of from 5° to 25° C., especially 10° to 15° C. The extrudate can then be run off or, if necessary, scraped or chipped off, the roller and conveyed direct to suitable milling equipment, for example a hammer mill or preferably a roll mill. Using a combined chill roller and roll mill assembly, it may be possible to perform both the cooling and milling operations in one piece of equipment.

Following milling, it is preferable to classify or screen the particulate extrudate, to obtain a particle size which is optimal for use or subsequent processing. Undersized particles could be recycled to the extrusion stage; oversized particles could be recycled to the milling stage.

The milling equipment is suitably such as to achieve particles of a granular consistency, having for example a diameter in the region of 250 micrometers. A solid formulation prepared in this manner has little associated dust once sieve-cut to cause particular handling or product loss problems.

For the extrusion itself, any suitable extrusion equipment may be utilised. Extruders consist, generally, of a cylindrical barrel in which materials are heated and moved through the barrel by means of at least one rotating screw. Thus, the action in the barrel is one of shearing, rubbing and kneading at elevated temperature. In this way, the pyrethroid and the polyvinylpyrrolidone become mixed on a molecular scale and under the combination of externally applied heat and the internal shear force, which creates more internal heat within the mixture, a solid solution of pyrethroid in the polyvinylpyrrolidone is formed.

Suitable extrusion equipment is a twin screw, co-rotating extruder, such as is used in the food processing, pharmaceutical and polymer processing industries. Typically, extrusion is carried out in a twin screw extruder having a barrel with a cooled feed zone and with at least one melt zone. For two or more melt zones, each melt zone is of a different temperature in accordance with a graduated temperature profile. The melt temperature or temperature profile is suitably such that the extrudate on leaving the extruder barrel has a temperature in the range of from 50° to 200° C. for example from 150° to 200° C., but preferably from 80° to 200° C. There may be several zones in the extruder barrel, for example from 4 to 9, each having a defined temperature usually obtained by the combination of external electrical heating of the barrel, internal shear forces and, if necessary, water cooling. The temperature of the mixed materials within the barrel is often significantly higher than the applied temperature in view of the heat generated by the internal shear force; to maintain a defined temperature for each zone, external cooling, e.g. by water, as well as heating may be required. The extruder may incorporate a die plate to aid subsequent extrudate processing, but in fact there is no need to have a die plate and if, for example, a chill roller or chill roller/mill assembly is also used, it is preferable that there should be no die plate on the machine. The extruder may also incorporate a separate preliminary mixing section, if needed.

Any pyrethroid can be formulated using the co-extrusion process described above provided that it dissolves in polyvinylpyrrolidone to form a solid solution and does not chemically decompose during extrusion. The temperature profile of the extrusion process will need to be adapted to operate at temperatures compatible with the fusion points of the pyrethroid and the polyvinylpyrrolidone. Preferably extrusian is carried out at or especially above the fusion point of the pyrethroid/polyvinylpyrrolidone mixture. Furthermore, the amount of pyrethroid used will depend on the degree to which it is soluble in the polyvinylpyrrolidone. Exceeding the solubility limit of pyrethroid in polyvinylpyrrolidone it is still possible to prepare a solid formulation but the dispersion and biological characteristics may be impaired. Naturally for each pyrethroid, such optimisation of operation temperature and ingredient proportions for the process can be carried out by routine experimentation. Suitably, a pyrethroid having a melting temperature in the range of from 60° C. to 200° C. is used.

Polyvinylpyrrolidone is a well known commercial product available in various forms from, for example, the companies BASF and ISP; the water-soluble polymer and its preparation is described in, inter alia, The Merck Index, 11th Edition, Monograph 7700. Suitable polyvinylpyrrolidone polymers for use in the present invention are any of the available forms, without restriction. Desirably they have a Fikentscher K value, see U.S. Pat. No. 2,706,701 or Cellulose-Chemie 13 (1932), pages 58 to 64 and 71 to 74, of in the range of from 10 to 100 reflecting a molecular weight of from 5,000 to 700,000. Preferred polyvinylpyrrolidone polymers have a K value of to 40, especially 25 to 35. The polymer is desirably a homopolymer of vinylpyrrolidone monomers, but may be used as a copolymer provided that at least 50% or more of the polymer units are vinyl pyrrolidone monomers.

The polyvinylpyrrolidone may be made in any conventional manner, for example by polymerisation initiated by hydrogen peroxide or an organic peroxide in a suitable solvent such as water or a suitable organic solvent.

Naturally, where the solid formulation is made by co-extrusion, the polyvinylpyrrolidone must fuse at the operating temperature of the extruder, and it may be necessary to select a compatible polyvinylpyrrolidone based on the melting point of the active ingredient and the consequent extrusion temperature required. For extrusion with alpha-cypermethrin, "Agrimer 30" a polyvinylpyrrolidone polymer available from ISP has been found to be very suitable. Agrimer 30 has a K value of 30. This polyvinylpyrrolidone has a glass transition temperature of 156° to 157° C.; when mixed with alpha-cypermethrin, which has a melting point of 72° C., a typical glass transition temperature of the mixture is of the order of 146° C. A suitable operating extrusion temperature or temperature profile for such mixtures is such that the extrudate, is a melt having a temperature of above 77° C. and desirably above 110° C. (as determined by routine experimentation); such mixtures have been satisfactorily extruded up to 185° C.

Polyvinylpyrrolidone prepared by polymerisation in water may often have a higher water content (of the order of 5% by weight); polyvinylpyrrolidone prepared by other means can also imbibe water from the atmosphere because of its hygroscopic nature. Where the solid formulation is made by co-extrusion, the water content of the polyvinylpyrrolidone prior to extrusion is not critical. Should polyvinylpyrrolidone having a water content of greater than say 3.5% by weight be used, and it is desired to have a low residual water content in the extrudate, preferably water vapour is drawn off under vacuum, for example by means of a vacuum pump, during extrusion. Thus, preferably, an extruder is used which has one or more vent ports, to vent moisture, associated with a vent port stuffer, to prevent loss of solid material through the vent port, and a vacuum pump to remove water vapour.

The minimum quantity of polyvinylpyrrolidone in the solid formulation is dependent upon the desired extent and rate of dispersion of the formulation in water. The quantity of polyvinylpyrrolidone present in the solid formulation is preferably greater than 50% w/w, more preferably in the range of from 50% w/w to 90% w/w, the most preferred range being from 60% w/w to 70% w/w.

In addition to polyvinylpyrrolidone and a pyrethroid insecticide, the solid formulation may comprise other components. Said solid formulation preferably includes effervescing means for rendering the solid formulation effervescent in water. Said means preferably includes an acid, for example, citric acid, and an alkali, for example an alkali metal carbonate or bicarbonate. Said solid formulation preferably also includes disintegration means for aiding disintegration of the solid formulation in water. A preferred disintegration means is cellulose, for example, microcrystalline cellulose sold under the Trade name AVICEL PH101. The solid formulation may also include surface active agents, corrosion inhibitors and/or stabilisers. In addition, the solid formulation may comprise one or more inert fillers. However, if the aforementioned other components or fillers are present in the solid formulation, the ratio of pyrethroid compound to polyvinylpyrrolidone is preferably in the range of from 1:1 to 1:5, most preferably from about 1:2 to 1:3.

Inclusion of a surface active agent in the solid formulation is not necessary to ensure a ready and rapid dispersion of the pyrethroid compound in water. However, examples of suitable surface active agents that may be included in the formulation are the sodium salts of xylene sulphonates, the sodium salts of alkylbenzenesulphonates, the sodium or calcium salts of polyacrylic acids and lignin sulphonic acids and sodium or calcium salts of carboxylic acids. A group of the most suitable surface active agents is the sodium lignosulfonates, for example the commercial product "VANISPERSE" (Trade Mark).

Suitable inert fillers for inclusion in the formulation include natural and synthetic clays and silicates, for example natural silicas such as diatomaceous earths; magnesium silicates, for example talcs; magnesium aluminium silicates, for example kaolinites, montmorillonites and micas; calcium carbonate, calcium sulphate; ammonium sulphate; synthetic calcium or aluminium silicates; elements, for example carbon and sulphur; natural and synthetic resins, for example coumarone resins, polyvinyl chloride, and styrene polymers and copolymers; solid polychlorophenols and solid fertilisers, for example superphosphates.

Any additional ingredients utilised in a co-extrusion of pyrethroid and polyvinylpyrrolidone will depend on the end use of the formulation and/or the main extrusion ingredients. Thus, for example, for extrusion of alpha-cypermethrin technical material, which is a racemic mixture of two cis-2-isomers as described above, the extrusion material must be rendered slightly acidic to prevent epimerisation or inversion of the cis-2-isomers to the cis-1-isomers. Suitably in the range of from 0.5 to 0.9 % m/m of an organic acid for example benzoic acid or, preferably, toluene sulphonic acid, is included in the ingredients for extrusion; useful results are also obtained from the incorporation of water soluble salts such as potassium hydrogen sulphate or sodium sulphate; potassium hydrogen sulphate is especially preferred.

Where the solid formulation includes other ingredients, for example effervescing means and/or disintegration means and/or surface active agents and/or corrosion inhibitors and/or stabilisers, said ingredients are preferably added after the co-extrusion, for example during the preparation of tablets from the extrudate.

The following examples illustrate the invention.

Certain terms used in the examples are explained below.

FASTAC is a trade name of Shell International Chemical Company for alpha-cypermethrin and is particularly a racemate comprising (S) ∝-cyano-3-phenoxybenzyl(1R)-cis-3-(2,2-dichloro-vinyl)-2,2 dimethylcyclopropanecarboxylate and (R)-∝-cyano-3-phenoxybenzyl(1S)-cis-3-(2,2-dichlorovinyl)-2,2-dimethylcyclo-propanecarboxylate.

Agrimer 30 is a trade name of ISP (Europe) Limited for polyvinylpyrrolidone;

Empicol LZ is a trade name of Albright & Wilson for sodium lauryl sulphate;

Avicel PH101 is a trade name of FMC Corporation for a microcrystalline cellulose;

Neosyl TS is a trade name of * for silica;

Sorbitol P300 is a sorbital supplied by Merck U.K.

EXAMPLE 1

Preparation of FASTAC/Polyvinylpyrrolidone Solid Formulation.

(a) Preparation of FASTAC/Polyvinylpyrrolidone Granules

A blend of the following powdered materials was mixed using a core blender:

|  | g/kg |
|---|---|
| FASTAC (100% m/m) | 400.0 |
| Potassium hydrogen sulphate | 4.8 |
| Agrimer 30 | 595.2 |

A sample of 5 kg of blended material was fed into an APV MP2030 twin screw co-rotating extruder, 25:1 L/D (length over diameter). A K-tron T20 volumetric feeder with agitated hopper was used to feed the extruder. The extruder barrel which was electrically heated and water Cooled was fitted with a vacuum pump via a vent port for use when a melt seal had formed. The barrel melt zone temperatures (nine in all) were set between 25 and 75 degrees centigrade (beginning to end of barrel) to 25 to 175 degrees centigrade (beginning to end of barrel).

A vacuum was drawn once a melt seal had formed in order to remove the water vapour that formed in the barrel from the residual moisture content of the polyvinylpyrrolidone. The extruder screws were constructed to give at least one conveyor section followed by a paddle shearing/mixing section. The extrudate was finally conveyed to the end of the barrel and extruded without a die-plate directly onto a chill roller (chilled with water at 4 degrees centigrade). The extrudate was rapidly cooled to a brittle glassy material on the rollers and removed as chips by pegs rotating near the surface of the larger of the two chill rollers. The chipped material was hammer milled and sieve cut to produce granules of approximately 250 micrometers.

(b) Preparation of FASTAC/Polyvinylpyrrolidone Tablets

Tablets having the following composition were prepared:

|  | g/kg |
|---|---|
| FASTAC (100% m/m) | 150.00 |
| Empicol LZ | 7.0 |
| Citric acid (anhydrous) | 210.00 |
| Potassium hydrogen carbonate | 290.00 |
| Potassium hydrogen sulphate | 1.80 |
| Avicel PH101 | 100.00 |
| Neosyl TS | 6.0 |
| Agrimer 30 | 223.20 |
| Sorbitol P300 | 12.0 |

The granules prepared in Example 1(a) were mixed with the other ingredients and then compressed to form tablets using a tabletting machine.

EXAMPLE 2

Assessments of Properties of Aqueous Dispersion of the Solid Formulation

The assessments involved a dipping trial of up to 803 Angus cross cattle in a conventional straight 20000 liters dip tank using tablets prepared in Example 1(b) which contain 150g/kg of active ingredient (alpha-cypermethrin).

The dip tank was initially cleaned and accurately calibrated using 200 liters calibrated drums filled with fresh water. The tank was then charged using 5kg of the tablets in 15000 liters of water in order to give a final target dipwash concentration of 50 ppm.

On contact with the water in the tank, the tablets immediately began to effervesce whilst moving down to the bottom of the tank. Approximately 1 minute later, the tablets resurfaced until completely dissolved.

The dip tank included a drip-race in order to ensure that a maximum amount of dipwash was returned to the tank from the dipped animals.

50 head of cattle were used to mix the dipwash after initial charging or replenishment.

Table 1 provides details of the dipping particulars.

Various assessments were undertaken as discussed further below.

(a) Stability of active ingredient in dip tank

The concentration of active ingredient in the dipwash was assessed at intervals. Results are provided in Table 2.

Table 3 provides details of the final concentration of active ingredient after most/all animals had been dipped in a particular week. In some cases, additional animals were dipped after the active ingredient concentration had been assessed as will be apparent from the results in Table 1.

(b) Efficacy of active ingredient in dip tank

The insecticidal activity of the dipwash was assessed, as follows.

Ten cattle infested with ticks (mainly *Hyalomma sp* and *Rhipicephalus evertsi evertsi*) were selected from the main herd and identified with numbered ear tags. The ticks on the animals were counted, at various intervals, in their known predilection site, which for both *Hyalomma sp* and *Rhipicephalus evertsi evertsi* is the perineum. Five of the ten cattle (numbered 1 to 5 in the following tables) were not treated with active ingredient. The other five (numbered 6 to 10 in the following tables) were treated under conditions described above with reference to Tables 1 to 3.

Results of the tick counts are provided in Tables 4 to 7. The reference "n/c" in the tables means that no count was undertaken. Also, it should be noted that Tables 4 and 6 relate to a count of unengorged ticks in the form of males and flat females; whereas Tables 5 and 7 relate to a count of partially and fully engorged females.

Discussion of properties of solid formulation/aqueous dispersion of solid formulation The following points have been noted from the assessments described above and from other assessments:

(i) The solid formulation dissolves rapidly in water;

(ii) The use of the solid formulation does not lead to any signs of irritation on the dipped animals;

(iii) The active ingredient remains in suspension in the dip tank liquid for at least two hours. This property was noted when the dipping process was delayed whilst waiting for the group of animals and is reflected in the active ingredient concentration in dipwash samples taken just prior to and after the waiting period;

(iv) Although the diptank liquid became contaminated with a considerable amount of organic material and other pollutants over the period of the assessments (ca. 26 weeks), the results of the assessment of active ingredient concentration in the dipwash indicate that the stability of the active ingredient is not affected by being delivered in the form of a solid formulation;

(v) The stripping rate of active ingredient is low; and (vi) The active ingredient is effective at combating ticks.

TABLE 1

| WEEK | REPLENISHMENT WATER (1) | REPLENISHMENT TABLETS (g) | DIPWASH VOLUME BEFORE (1) | DIPWASH VOLUME AFTER (1) | TOTAL ANIMALS DIPPED BY END OF WEEK | TOTAL DIPWASH REMOVED (1) | AVERAGE DIPWASH REMOVED PER ANIMAL (1) |
|---|---|---|---|---|---|---|---|
| 0 | *15000 | *5000 | 15000 | 13800 | 601 | 1200 | 2.00 |
| 1 | — | — | 13000 | 11400 | 628 | 1600 | 2.55 |
| 2 | 3600 | 1200 | 15000 | 13550 | 803 | 1450 | 1.81 |
| 3 | — | — | 13500 | 12200 | 675 | 1300 | 1.93 |
| 4 | 2900 | 936 | 15000 | 13900 | 664 | 1100 | 1.66 |
| 5 | — | — | 13400 | 12000 | 642 | 1400 | 2.18 |
| 7 | 4000 | 1326 | 15000 | 13300 | 678 | 1700 | 2.51 |
| 9 | 900 | 299 | 14200 | 12600 | 715 | 1600 | 2.24 |
| 11 | 2400 | 800 | 15000 | 13150 | 692 | 1850 | 2.67 |
| 14 | 2400 | 800 | 15000 | 12600 | 698 | 2400 | 3.44 |
| 16 | 1650 | 800 | 15000 | 12900 | 620 | 2100 | 3.39 |
| 19 | — | — | 12500 | 11800 | 185 | 700 | 3.78 |
| 22 | 3600 | 1200 | 15000 | 14400 | 158 | 600 | 3.80 |
| 25 | — | — | 13800 | 13200 | 148 | 600 | 4.05 |

TABLE 2

| NO. OF ANIMALS DIPPED | 0 | 1 | 2 | 3 | 4 | 5 | 7 | 9 | 11 | 14 | 16 | 19 | 22 |
|---|---|---|---|---|---|---|---|---|---|---|---|---|---|
| 0 | 44 | 49 | 43 | 45 | 41 | 47 | 56 | 44 | 43 | 53 | 51 | 42 | 48 |
| 50 | 45 | 49 | 46 | 47 | 42 | 41 | 47 | 43 | 42 | 54 | 53 | 38 | 46 |
| 100 | 43 | 48 | 48 | 48 | 40 | 40 | 50 | 42 | 52 | 56 | 53 | — | 46 |
| 150 | 44 | 48 | 44 | 46 | 38 | 35 | — | 40 | 50 | 54 | 52 | 38 | 45 |
| 200 | 42 | 46 | 42 | 46 | 38 | 36 | 50 | 42 | 53 | 52 | 50 | — | — |
| 250 | 42 | 46 | 40 | 44 | 37 | 36 | 49 | 41 | 51 | 48 | 50 | — | — |
| 300 | 42 | 45 | 38 | 44 | 38 | 38 | 48 | 41 | 51 | 54 | 48 | — | — |
| 350 | 43 | 45 | 37 | 42 | 38 | 38 | 48 | 40 | 50 | 52 | 48 | — | — |
| 400 | 38 | 45 | 35 | 43 | 38 | 30 | — | 40 | 50 | 52 | 50 | — | — |
| 450 | 39 | 44 | 33 | 42 | 38 | 30 | 43 | 40 | 49 | 47 | 50 | — | — |
| 500 | 36 | 43 | 32 | 41 | 35 | 27 | 42 | 40 | 45 | 39 | 49 | — | — |
| 550 | 35 | 42 | 32 | 39 | 35 | 27 | 41 | 37 | 45 | 39 | 48 | — | — |

TABLE 3

| | WEEK OF DIPPING | | | | | | | | | | | | |
|---|---|---|---|---|---|---|---|---|---|---|---|---|---|
| | 0 | 1 | 2 | 3 | 4 | 5 | 7 | 9 | 11 | 14 | 16 | 19 | 22 |
| Final active ingredient (alpha-cypermethrin) concentration in parts per million | 35 | 41 | 32 | 39 | 15 | 28 | 40 | 32 | 41 | 36 | 47 | 38 | 45 |
| Total number of animals dipped when concentration assessed | 550 | 578 | 803 | 675 | 664 | 642 | 600 | 665 | 642 | 648 | 620 | 185 | 158 |

TABLE 4

| MEAN TICK COUNTS - HYALLOMA spp. MALES AND FLAT FEMALES | | | | | | | | | | | | |
|---|---|---|---|---|---|---|---|---|---|---|---|---|
| | UNTREATED CONTROL ANIMALS | | | | | | ALPHA-CYPERMETHRIN TREATED ANIMALS | | | | | |
| WEEK | 1 | 2 | 3 | 4 | 5 | MEAN | 6 | 7 | 8 | 9 | 10 | MEAN |
| 0 | 15 | 8 | 23 | 3 | 16 | 13.0 | 21 | 15 | 9 | 9 | 17 | 14.2 |
| 1 | 13 | n/c | 27 | 7 | 30 | 19.3 | 0 | 0 | 2 | 0 | 6 | 1.6 |
| 2 | 15 | 20 | 9 | 8 | 21 | 14.6 | 0 | 0 | 0 | 0 | 0 | 0.0 |
| 3 | 16 | 0 | 7 | 3 | 13 | 7.8 | 0 | 0 | n/c | 0 | 0 | 0.0 |
| 4 | 15 | n/c | 6 | 1 | 8 | 7.5 | 0 | 0 | 0 | 0 | 0 | 0.0 |
| 5 | 9 | n/c | 1 | 0 | 1 | 2.8 | 0 | 0 | 0 | 0 | 0 | 0.0 |
| 7 | 1 | n/c | 0 | 0 | 0 | 0.3 | 0 | 0 | 0 | 0 | 0 | 0.0 |
| 9 | 0 | n/c | 0 | 0 | 0 | 0.0 | 0 | 0 | 0 | 0 | 0 | 0.0 |

TABLE 5

| MEAN TICK COUNTS - HYALLOMA spp. ENGORGING FEMALES (1/4 F, 1/2 F & FULL) | | | | | | | | | | | | |
|---|---|---|---|---|---|---|---|---|---|---|---|---|
| | UNTREATED CONTROL ANIMALS | | | | | | ALPHA-CYPERMETHRIN TREATED ANIMALS | | | | | |
| WEEK | 1 | 2 | 3 | 4 | 5 | MEAN | 6 | 7 | 8 | 9 | 10 | MEAN |
| 0 | 4 | 4 | 5 | 4 | 7 | 4.9 | 8 | 2 | 0 | 1 | 7 | 3.6 |
| 1 | 2 | n/c | 8 | 1 | 3 | 3.5 | 1 | 0 | 0 | 0 | 3 | 0.8 |
| 2 | 0 | 1 | 0 | 0 | 1 | 0.4 | 0 | 0 | 0 | 0 | 1 | 0.2 |
| 3 | 0 | 0 | 0 | 0 | 0 | 0.0 | 0 | 0 | n/c | 0 | 0 | 0.0 |
| 4 | 0 | n/c | 0 | 0 | 0 | 0.0 | 0 | 0 | 0 | 0 | 0 | 0.0 |
| 5 | 0 | n/c | 0 | 0 | 0 | 0.0 | 0 | 0 | 0 | 0 | 0 | 0.0 |
| 7 | 0 | n/c | 0 | 0 | 0 | 0.0 | 0 | 0 | 0 | 0 | 0 | 0.0 |
| 9 | 0 | n/c | 0 | 0 | 0 | 0.0 | 0 | 0 | 0 | 0 | 0 | 0.0 |

TABLE 6

MEAN TICK COUNTS - *R. evertsi evertsi* MALES AND FLAT FEMALES

| WEEK | UNTREATED CONTROL ANIMALS | | | | | | ALPHA-CYPERMETHRIN TREATED ANIMALS | | | | | |
|---|---|---|---|---|---|---|---|---|---|---|---|---|
| | 1 | 2 | 3 | 4 | 5 | MEAN | 6 | 7 | 8 | 9 | 10 | MEAN |
| 0 | 15 | 8 | 23 | 3 | 16 | 13.0 | 21 | 15 | 9 | 9 | 17 | 14.2 |
| 1 | 13 | n/c | 27 | 7 | 30 | 19.3 | 0 | 0 | 2 | 0 | 6 | 1.6 |
| 2 | 15 | 20 | 9 | 8 | 21 | 14.6 | 0 | 0 | 0 | 0 | 0 | 0.0 |
| 3 | 16 | 0 | 7 | .3 | 13 | 7.8 | 0 | 0 | n/c | 0 | 0 | 0.0 |
| 4 | 15 | n/c | 6 | 1 | 8 | 7.5 | 0 | 0 | 0 | 0 | 0 | 0.0 |
| 5 | 9 | n/c | 1 | 0 | 1 | 2.8 | 0 | 0 | 0 | 0 | 0 | 0.0 |
| 7 | 1 | n/c | 0 | 0 | 0 | 0.3 | 0 | 0 | 0 | 0 | 0 | 0.0 |
| 9 | 0 | n/c | 0 | 0 | 0 | 0.0 | 0 | 0 | 0 | 0 | 0 | 0.0 |

TABLE 7

MEAN TICK COUNTS - *R. evertsi evertsi* ENGORGING FEMALES (1/4 F, 1/2 F & FULL)

| WEEK | UNTREATED CONTROL ANIMALS | | | | | | ALPHA-CYPERMETHRIN TREATED ANIMALS | | | | | |
|---|---|---|---|---|---|---|---|---|---|---|---|---|
| | 1 | 2 | 3 | 4 | 5 | MEAN | 6 | 7 | 8 | 9 | 10 | MEAN |
| 0 | 4 | 4 | 5 | 4 | 7 | 4.8 | 8 | 2 | 0 | 1 | 7 | 3.6 |
| 1 | 2 | n/c | 8 | 1 | 3 | 3.5 | 1 | 0 | 0 | 0 | 3 | 0.8 |
| 2 | 0 | 1 | 0 | 0 | 1 | 0.4 | 0 | 0 | 0 | 0 | 1 | 0.2 |
| 3 | 0 | 0 | 0 | 0 | 0 | 0.0 | 0 | 0 | n/c | 0 | 0 | 0.0 |
| 4 | 0 | n/c | 0 | 0 | 0 | 0.0 | 0 | 0 | 0 | 0 | 0 | 0.0 |
| 5 | 0 | n/c | 0 | 0 | 0 | 0.0 | 0 | 0 | 0 | 0 | 0 | 0.0 |
| 7 | 0 | n/c | 0 | 0 | 0 | 0.0 | 0 | 0 | 0 | 0 | 0 | 0.0 |
| 9 | 0 | n/c | 0 | 0 | 0 | 0.0 | 0 | 0 | 0 | 0 | 0 | 0.0 |

We claim:

1. A formulation which contains a melt extrudate consisting essentially of polyvinylpyrrolidone homopolymer having a K value of about 20 to 40 and an insecticidally effective amount of a pyrethroid insecticide, wherein the polyvinylpyrrolidone in the extrudate is present in the amount of from about 50 to 90 percent w/w and wherein a solid solution of pyrethroid in said polyvinylpyrrolidone is formed.

2. An aqueous dispersion comprising the formulation of claim 1 and water.

3. The aqueous dispersion according to claim 2 for the treatment of animals.

4. A method of treating or protecting animals from insects comprising administering to the animals a liquid formulation of claim 1.

5. A method of combating insects harmful to animals comprising contacting the insects with a liquid formulation of claim 1.

6. The formulation according to claim 1 for the treatment of animals.

7. A formulation which contains a melt extrudate consisting essentially of polyvinylpyrrolidone homopolymer having a K value of about 20 to 40 and an insecticidally effective amount of alpha-cypermethrin, wherein the polyvinylpyrrolidone in the extrudate is present in the amount of from about 50 to 90 percent w/w and wherein a solid solution of alpha-cypermethrin in said polyvinylpyrrolidone is formed.

8. The formulation of claim 7 for the treatment of animals.

9. A formulation containing a melt extrudate having a glass transition temperature of greater than about 75° C. to less than about 155° C. consisting essentially of a polyvinylpyrrolidone homopolymer having a K value of about 20 to 40 and an insecticidally effective amount of a pyrethroid insecticide, wherein the polyvinylpyrrolidone in the extrudate is present in the amount of from about 50 to 90 percent w/w and wherein a solid solution of pyrethroid in said polyvinylpyrrolidone is formed.

10. The formulation of claim 9 further containing an agent for rendering said formulation effervescent in water.

11. The formulation of claim 10 wherein the agent is selected from the group consisting of an acid and a base.

12. The formulation of claim 9 further containing an agent for aiding disintegration of said formulation in water.

13. The formulation of claim 9 having at least one ingredient selected from the group consisting of a surface active agent, corrosion inhibitor, stabilizer and inert filler.

14. A method of treating or protecting animals from insects comprising administering to the animals a liquid formulation of claim 9.

15. A method of combating insects harmful to animals comprising contacting the insects with a liquid formulation of claim 9.

16. A formulation containing a melt extrudate consisting essentially of a polyvinylpyrrolidone homopolymer having a K value of about 20 to 40 and an insecticidally effective amount of a pyrethroid insecticide having the formula:

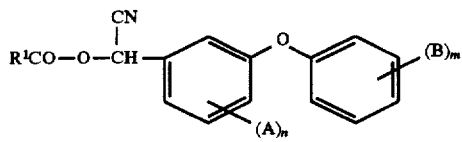

where A and B independently represent a halogen atom or a methyl group; n is 0, 1 or 2; m is 0, 1 or 2; and $R^1$ represents a group of formula:

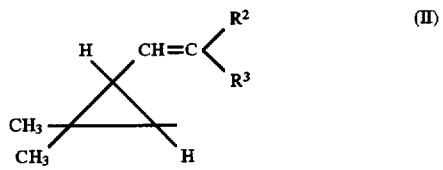

where $R^2$ and $R^3$ independently represent a hydrogen or halogen atom, or an optionally substituted $C_{1-4}$ alkyl group; or $R^1$ represents a group of formula:

where $R^4$ represents a phenyl group optionally substituted by one or more substituents independently selected from halogen atoms, or $C_{1-4}$ alkyl, $C_{1-4}$ alkylthio, $C_{1-4}$ alkoxy, nitro and methylenedioxy groups, wherein the polyvinylpyrrolidone in the extrudate is present in the amount of from about 50 to 90 percent w/w and wherein a solid solution of pyrethroid in said polyvinylpyrrolidone is formed.

17. The formulation of claim 16 wherein either or both A and B represent a halogen atom.

18. The formulation of claim 16 wherein n is 0 or 1.

19. The formulation of claim 16 wherein m is 0.

20. The formulation of claim 16 further containing an agent for rendering said formulation effervescent in water.

21. The formulation of claim 20 wherein the agent is selected from the group consisting of an acid and a base.

22. The formulation of claim 16 further containing an agent for aiding disintegration of said formulation in water.

23. The formulation of claim 16 having at least one ingredient selected from the group consisting of a surface active agent, corrosion inhibitor, stabilizer and inert filler.

24. A method of treating or protecting animals from insects comprising administering to the animals a liquid formulation of claim 16.

25. A method of combating insects harmful to animals comprising contacting the insects with a liquid formulation of claim 16.

26. A solid solution consisting essentially of a melt extrudate containing a polyvinylpyrrolidone homopolymer having a K value of about 20 to 40 and an insecticidally effective amount of alpha-cypermethrin dissolved in said polyvinylpyrrolidone, the polyvinylpyrrolidone being present in the extrudate in an amount of at least about 50 percent w/w.

27. The solid solution of claim 26 for the treatment of animals.

28. A formulation consisting essentially of a melt extrudate solid solution having a glass transition temperature of greater than about 75° C. to less than about 155° C., the extrudate containing a polyvinylpyrrolidone homopolymer having a K value of about 20 to 40 and an insecticidally effective amount of a pyrethroid insecticide dissolved in said polyvinylpyrrolidone, the polyvinylpyrrolidone being present in the extrudate in an amount of at least about 50 percent w/w.

29. The formulation of claim 28 further containing an agent for rendering said formulation effervescent in water.

30. The formulation of claim 29 wherein the agent is selected from the group consisting of an acid and a base.

31. The formulation of claim 28 further containing an agent for aiding disintegration of said formulation in water.

32. The formulation of claim 28 having at least one ingredient selected from the group consisting of a surface active agent, a corrosion inhibitor, a stabilizer and an inert filler.

33. A method of treating or protecting animals from insects comprising administering to the animals a liquid formulation of claim 28.

34. A method of combating insects harmful to animals comprising contacting the insects with a liquid formulation claim 28.

35. A formulation which contains a melt extrudate solid solution consisting essentially of a Polyvinylpyrrolidone homopolymer having a K value of about 20 to 40 and an insecticidally effective amount of a pyrethroid insecticide having the formula:

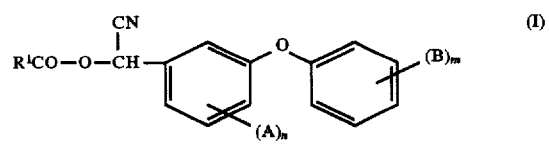

where A and B independently represent a halogen atom or a methyl group; n is 0, 1 or 2; m is 0, 1 or 2; and $R^1$ represents a group of formula:

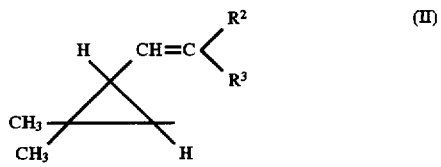

where $R^2$ and $R^3$ independently represent a hydrogen or halogen atom, or an optionally substituted $C_{1-4}$ alkyl group; or $R^1$ represents a group of formula:

where $R^4$ represents a phenyl group optionally substituted by one or more substituents independently selected from halogen atoms, or $C_{1-4}$ alkyl, $C_{1-4}$ alkylthio, $C_{1-4}$ alkoxy, nitro and methylenedioxy groups; wherein the pyrethroid insecticide is dissolved in said polyvinylpyrrolidone homopolymer and said polyvinylpyrrolidone homopolymer is present in the extrudate in an amount of at least about 50 percent w/w.

36. The formulation of claim 35 wherein either or both A and B represent a halogen atom.

37. The formulation of claim 35 wherein n is 0 or 1.

38. The formulation of claim 35 wherein m is 0.

39. The formulation of claim 35 further containing an agent for rendering said formulation effervescent in water.

40. The formulation of claim 39 wherein the agent is selected from the group consisting of an acid and a base.

41. The formulation of claim 35 further containing an agent for aiding disintegration of said formulation in water.

42. The formulation of claim 35 having at least one ingredient selected from the group consisting of a surface active agent, a corrosion Inhibitor, a stabilizer and an inert filler.

43. A method of treating or protecting animals from insects comprising administering to the animals a liquid formulation of claim 35.

44. A method of combating insects harmful to animals comprising contacting the insects with a liquid formulation of claim 35.

* * * * *

UNITED STATES PATENT AND TRADEMARK OFFICE
CERTIFICATE OF CORRECTION

PATENT NO. : 5,711,956
DATED : January 27, 1998
INVENTOR(S) : David J. Wedlock et al.

It is certified that error appears in the above-identified patent and that said Letters Patent are hereby corrected as shown below:

Title page [73], Assignee: should read -- Shell Research Limited

Signed and Sealed this

Seventeenth Day of April, 2001

Attest:

NICHOLAS P. GODICI

Attesting Officer      Acting Director of the United States Patent and Trademark Office